United States Patent [19]
Tatum et al.

[11] Patent Number: 5,908,397
[45] Date of Patent: Jun. 1, 1999

[54] DEVICE FOR POSITIONING AND SUPPORTING LEGS DURING CASTING

[75] Inventors: Danny L. Tatum; James L. Lewis, both of Chester, Calif.

[73] Assignee: Cascade Orthopedic Supply, Inc., Chester, Calif.

[21] Appl. No.: 08/825,208

[22] Filed: Mar. 27, 1997

[51] Int. Cl.$^6$ ........................................ A61F 5/00
[52] U.S. Cl. .................. 602/5; 602/23; 128/845
[58] Field of Search ................... 602/6, 23, 24, 602/25, 27–29, 39, 5; 128/882, 845; 36/88, 93; 5/651; 482/52, 53, 7–9, 80, 907, 145, 146; 606/241, 242

[56] References Cited

U.S. PATENT DOCUMENTS

| | | | |
|---|---|---|---|
| 3,892,231 | 7/1975 | Tummillo | 602/24 |
| 4,433,678 | 2/1984 | Spann | 602/24 |
| 5,147,286 | 9/1992 | Meals | 602/24 |
| 5,148,800 | 9/1992 | Pecheux | 482/79 X |
| 5,267,949 | 12/1993 | De La Torre et al. | 128/882 X |
| 5,277,681 | 1/1994 | Holt | 482/112 |
| 5,470,310 | 11/1995 | Sutcliffe | 602/24 |
| 5,499,958 | 3/1996 | Hess | 482/79 |
| 5,522,792 | 6/1996 | Bassett et al. | 602/24 X |

*Primary Examiner*—Richard J. Apley
*Assistant Examiner*—Denise Pothier
*Attorney, Agent, or Firm*—Heisler & Associates

[57] ABSTRACT

A casting device 10 for positioning and supporting legs L and other lower extremities of a patient P is provided. The casting device 10 includes a center frame rail 20 which adjustably supports a series of components thereon. A gluteal support section 40 is adjustably connected to the center frame rail 20 through a slit 30. A sub-perineal spacer 50 having a desired minimum width for spacing between legs L of the patient P is slidably supported along the slit 30 of the center frame rail 20. A knee support section 70 is also slidably supported by the slit 30 of the center frame rail 20. A stance width section 90 is adjustably attached to the center frame rail 20 and supports foot positioning supports 100 extending upward therefrom. Each foot positioning support 100 is adjustable to modify a stance width W of the casting device 10. Each foot positioning support 100 includes a foot shell 120 which can be angled at a dorsiflexion angle, by inserting a dorsiflexion wedge 130 between each foot shell 120 and each foot positioning support 100. The foot positioning supports 100 are oriented vertically and angled away from each other by a toe out angle a. Ankle restraint straps 110 are provided to securely hold feet F of the patient P adjacent the foot shells 120 during use of the casting device 10. A pad 150 is provided adjacent the gluteal support section 40 to provide a comfortable surface for the torso and head of the patient P. With the patient P resting upon the casting device 10 and securely attached to the foot positioning supports 100 through the ankle restraint straps 110, casting materials can be applied to the lower extremities of the patient P to provide a cast having optimal characteristics for formation of a cast which leads to formation and manufacture of orthotic devices such as those particularly useful to paraplegics in gaining upright mobility.

21 Claims, 5 Drawing Sheets

DEVICE FOR POSITIONING AND SUPPORTING LEGS DURING CASTING

FIELD OF THE INVENTION

The following invention relates to casting devices used in the fitting and manufacture of braces and other orthotics for use by paraplegics to stand and walk. More specifically, this invention relates to casting devices for accurately positioning and supporting the lower extremities of a paraplegic during the casting process so that braces and other orthotics can be manufactured to specifications closely matching the physical dimensions of the paraplegic. One such orthotic brace device for which this casting device is particularly suitable is the "Up & About" system distributed in the United States by Cascade Orthopedic Supply, Inc. of Chester, Calif.

BACKGROUND OF THE INVENTION

Many paraplegics have sufficient upper body strength to effectively perform most of the daily tasks experienced by a healthy person having a relatively sedentary job, such as jobs which primarily involve sitting and a movement about an office or similar environment. By providing such paraplegics with orthotics and braces which allow the paraplegic to use their upper body muscles to stand and walk, such paraplegics are allowed to participate in an even larger range of activities enjoyed by others. One such orthotic device which has been particularly effective in allowing paraplegics to stand and move in an upright manner is the "Up & About" device distributed by Cascade Orthopedic Supply, Inc.

One problem encountered in the use of such orthotics is that the device must be manufactured to very precise dimensions exhibited by the paraplegic. If the orthotic device is not effectively tailored to the paraplegic, excessive discomfort and inoperability will result, either making the orthotic unusable or increasing a likelihood that the paraplegic will choose not to utilize the orthotic device and remain confined to a wheel chair or remain at home.

To effectively construct the orthotic device to match the individual dimensions of the paraplegic, known lower extremity casting techniques are utilized to make casts of each of the paraplegic's legs. These casts are then used during the custom fabrication and assembly process utilized in manufacturing each orthotic device to ensure that the orthotic device properly fits the paraplegic. Existing casting techniques are generally only marginally effective in allowing the orthotic device to meet minimal standards of fit. Such devices are often far from optimal largely because the paraplegic's lower extremities are not held in the precise position needed for the casts of the paraplegic's lower extremities to have the configuration necessary for optimum fitting and construction of the orthotic device.

Accordingly, a need exists for a casting device which can securely position and support the lower extremities of a paraplegic during the casting process which will cause the casts of the paraplegics lower extremities to match an optimum configuration for fitting of the orthotic device. Through use of such a casting device, orthotic devices can be constructed for paraplegics which provide such a perfect fit to the paraplegic that the paraplegic will be highly motivated to utilize the orthotic device, thus enhancing the benefit the paraplegic will enjoy from the use of the orthotic device.

SUMMARY OF THE INVENTION

The casting device of this invention provides a framework which can be oriented upon a treatment table or other level surface to support the entire body of the paraplegic, and especially the lower extremities of the paraplegic in the precise position needed for accurate casting of the lower extremities of the paraplegic or other patient. A foot positioning support is provided at a location adjacent each foot of the patient. Each foot positioning support is coupled to a stance width section which in turn is adjustably supported upon a center frame rail. Foot shells are attached to each foot positioning support which have a contour generally matching that of each foot of the patient.

The foot positioning supports and foot shells are configured such that the foot shells exhibit a toe out configuration which matches a toe out configuration necessary for optimal configuration of the orthotic device. A dorsiflexion wedge is positioned between each foot positioning support and each foot shell, causing a toe end of each foot shell to be closer to the head of the patient than a heel end of each foot shell during the casting process. This dorsiflexion angle is necessary to optimize the orientation of the feet of the patient when forming the casts of the patient's lower extremities so that when the orthotic device is in use the patient's feet will have the correct orientation for optimal use of the orthotic device.

A sub-perineal spacer is supported along the center frame rail at a position between 10 millimeters and 30 millimeters from the perineum of the patient. The sub-perineal spacer exhibits a width similar to a minimum acceptable width between the legs of the patient at this distance from the perineum, for proper fitting of the orthotic device. A gluteal support section is also attached to the center frame rail for support of the patient. A rectangular pad is attached to the gluteal support section and provides comfortable support for the torso of the patient during the casting procedure. A knee support section can also be connected to the center frame rail.

The gluteal support section, knee support section, and stance width section provide for elevation of the lower extremities of the patient above the horizontal surface upon which the casting device rests. Thus, clearance is provided for location of casting material, such as plaster bandages, to and around the legs of the patient.

Straps are provided on the foot positioning supports to secure the feet of the patient within the foot shells. The foot positioning supports can be slid within the slits on the stance width section to make sure that the stance width of the patient is optimal during the casting procedure. The entire casting device can be easily assembled, disassembled and adjusted through use of various different threaded bolts, slots and nuts to allow the casting device to be easily stored and reerected for reuse with a patient having different lower extremity dimensions.

OBJECTS OF THE INVENTION

Accordingly, a primary object of the present invention is to provide a device for positioning and supporting legs of a paraplegic or other patient during casting of the lower extremities of the patient for optimal formation of orthotic devices to be used by the patient.

Another object of the present invention is to provide a casting device which can hold the feet and legs of a patient in a position having a toe out configuration and a negative dorsiflexion angle with toes of the patient closer to the head than heels of the patient and with an optimal stance width.

Another object of the present invention is to provide a casting device which comfortably supports a person thereon during casting of the lower extremities of the person.

Another object of the present invention is to provide a casting device which positions legs of a person with sufficient spacing there between for casts of the lower extremities to be useful in forming orthotic devices from the casts which require such clearance between the legs of the person.

Another object of the present invention is to provide a casting device which is adjustable to match the dimensions of the lower extremities of persons having a broad range of sizes and deformities.

Another object of the present invention is to provide a method for restraining and positioning legs of a patient during casting thereof to optimize the formation of casts as an initial step in forming orthotic devices.

Another object of the present invention is to provide a casting apparatus which can be readily erected and collapsed for transport and storage.

Another object of the present invention is to provide a casting apparatus which is formed from high strength materials which are easily cleaned for treatment of multiple different patients.

Other further objects of the present invention will become apparent from a careful reading of the included description and drawing figures as well as the included claims.

DESCRIPTION OF THE PREFERRED EMBODIMENT

Figure 1:
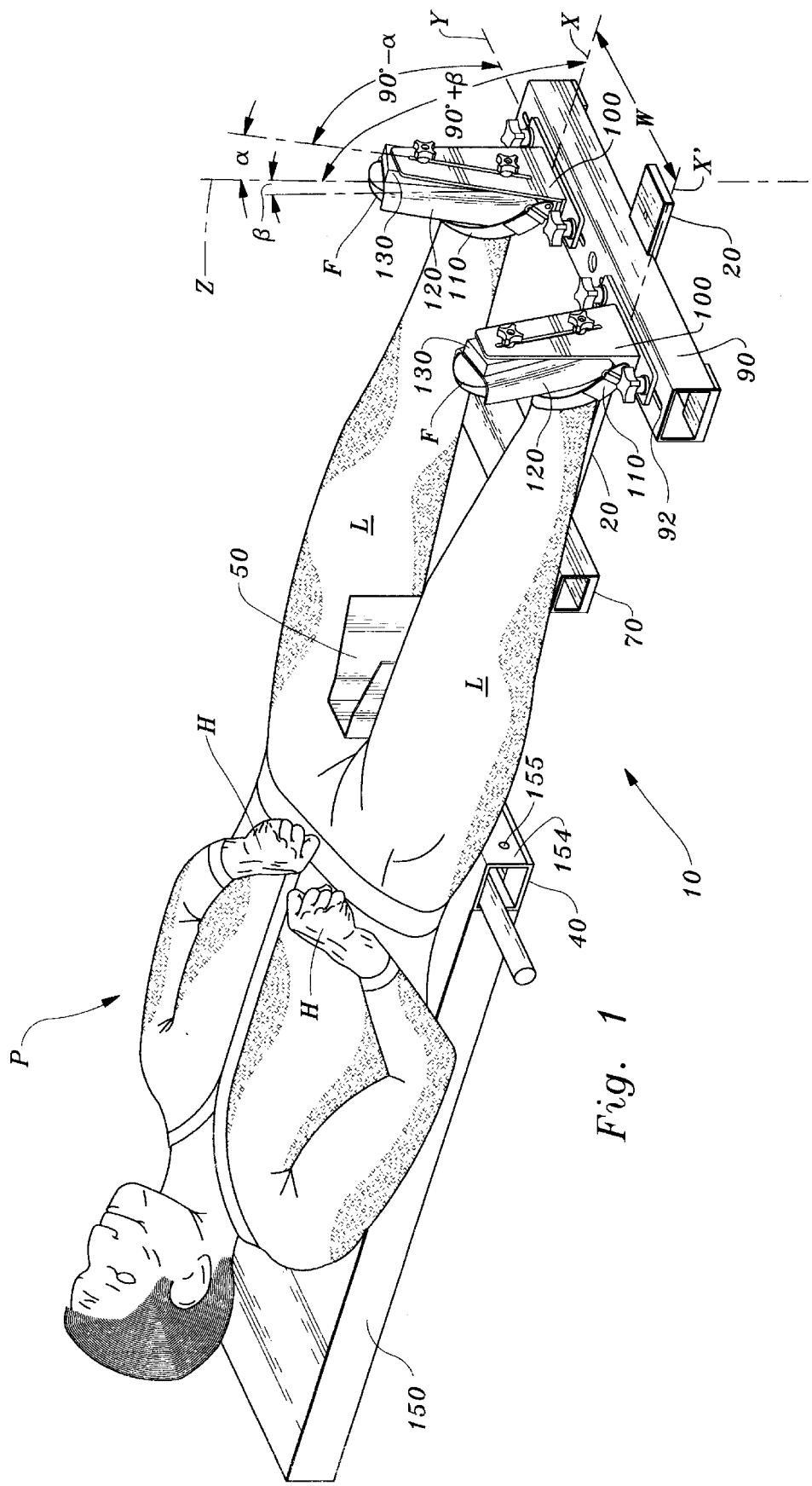
FIG. 1 is a perspective view of the casting device of this invention in use with a person resting thereon.

Referring to the drawings, wherein like reference numerals represent like parts throughout the various drawing figures, reference numeral 10 is directed to a preferred embodiment of a device for positioning and supporting legs during casting. It is understood that while this embodiment is currently believed to provide the best mode for practicing this invention, that other embodiments could also be provided which are deemed to be within the scope of the included claims. The casting device 10 is placed on a substantially flat surface and a patient P who is to have casts made of his/her legs L lies on top of the casting device 10. The feet F of the patient P are placed on adjacent foot positioning supports 100 which are supported upon a stance width section 90 which in turn is supported upon a center frame rail 20 resting upon the flat surface. The torso of the patient P rests upon a pad 150 which is attached to a gluteal support section 40 which in turn is supported by the central frame rail 20. A sub-perineal spacer 50 is oriented between the legs L of the patient P to assure that the legs L are in proper position during casting of the legs L. The casting device 10 assures that the legs L and other lower extremities of the patient P are in the optimal position for casting of the lower extremities of the patient P, especially for making casts of a paraplegic's lower extremities for optimal construction of an orthotic device, such as the "Up & About" orthotic device distributed by Cascade Orthopedic Supply, Inc. of Chester, Calif.

Figure 2:
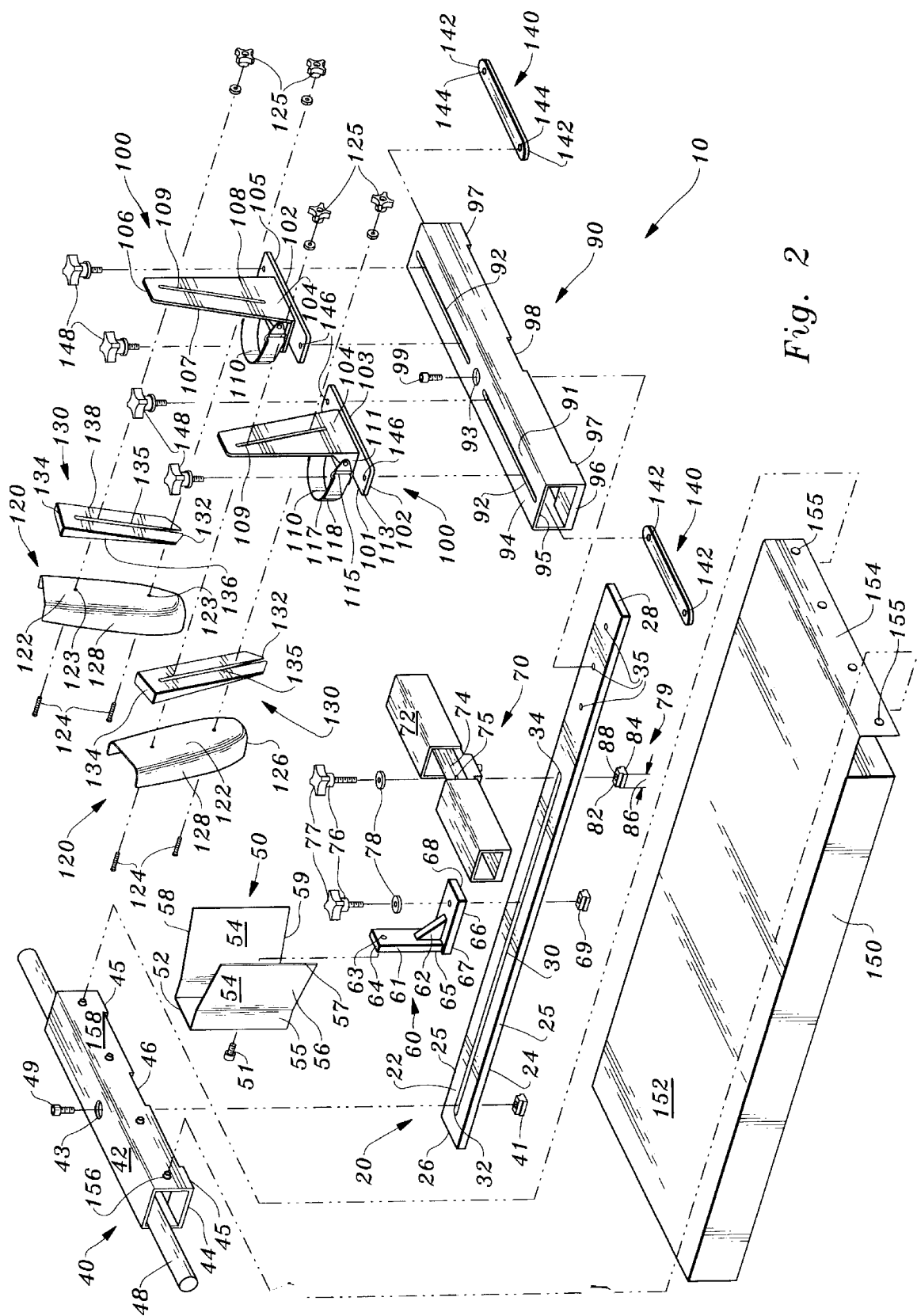
FIG. 2 is an exploded parts view of the casting apparatus of this invention.
Figure 3:
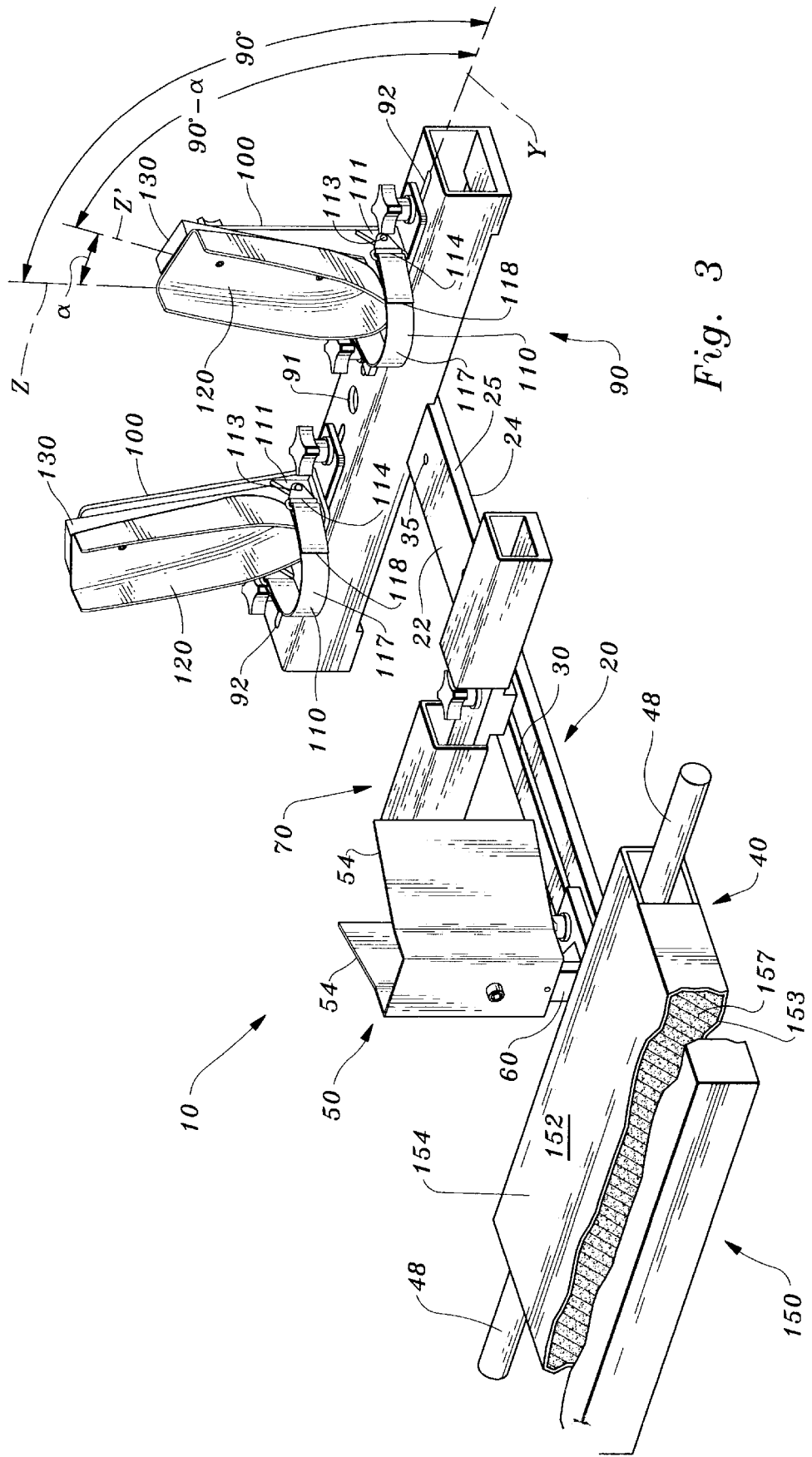
FIG. 3 is a perspective view of the casting apparatus of this invention without a person resting thereon.

In essence, and with particular reference to FIGS. 1 and 3, the casting device 10 provides a series of different components all adjustably locatable upon the center frame rail 20 and resting upon a substantially flat, preferably horizontal surface. The center frame rail 20 includes a slit 30 and a series of lower threaded holes 35 to which different components can be attached and detached at various different positions along the center frame rail 20. A gluteal support section 40 is adjustably secured to the center frame rail 20 through the slit 30. The gluteal support section 40 features a top wall 42 which provides support for a mid-portion of a patient P, resting upon the casting device 10. The gluteal support section 40 also includes snaps 156 (FIG. 2) on a lower wall 158 which are complemental to snaps 155 on an overhanging shroud 154 connected to a large rectangular pad 150. The pad 150 is thus secured in position relative to the gluteal support section 40 and provides a large surface for support of the torso and head of the patient P during use of the casting device 10.

A sub-perineal spacer 50 is coupled to the center frame rail 20 through a sub-perineal carrier 60, adjustably attached to the slit 30 of the center frame rail 20. The sub-perineal spacer 50 has a lateral width between side flanges 54 which establishes a preferred spacing between the legs L of the patient P at a location just below the perineum of the patient P. Different sizes of sub-perineal spacers 50 are provided (i.e. child, adult, adult wide) so that a spacer 50 of appropriate size for the patient P can be utilized. A knee support section 70 is adjustably attached to the center frame rail 20 through the slit 30. The knee support section 70 provides support for mid-portions of the legs L of the patient P, near the knees of the patient P. The knee support section enhances comfort for the patient P and assures that the legs L are in proper position during casting.

A stance width section 90 is secured to the center frame rail 20 through one of the lower threaded holes 35. The stance width section 90 features a top plate 91 which supports two foot positioning supports 100 thereon. Each foot positioning support 100 is adjustably locatable laterally upon the stance width section 90 by sliding along a pair of lateral slits 92. Each foot positioning support 100 extends vertically upward perpendicular to the center frame rail 20. A foot shell 120 is slidably attachable to each foot positioning support 100 on a side thereof closest to the gluteal support section 40 and pad 150. The foot shells 120 are contoured to allow the feet F of the patient P to rest within the foot shells 120 when the patient P is resting upon the casting device 10. Ankle restraint straps 110 are provided which can pass over ankles of the patient P to secure the feet F of the patient P within the foot shells 120 and adjacent the foot positioning supports 100.

A dorsiflexion wedge 130 is located between each foot shell 120 and each foot positioning support 100. The dorsiflexion wedge 130 is adjustably located between the foot shell 120 and the foot positioning support 100 to provide a dorsiflexion angle $\beta$, causing the toes of the patient P to be closer to the head of the patient P then are the heels of the patient P. The foot positioning supports 100 and foot shells 120 are also configured to cause the feet F of the patient P to exhibit a toe out angle $\alpha$ such that the toes of the patient P are further apart than are the heels of the patient P.

Once the casting device 10 has been configured appropriately for the dimensions of the particular patient P, the patient P is placed upon the casting device 10. Final minor adjustments of the casting device 10 can then be made and then the lower extremities of the patient P are cast while the lower extremities of the patient P are restrained by the casting device 10. In this way, precise casts having the optimal configuration are facilitated.

Figure 4:
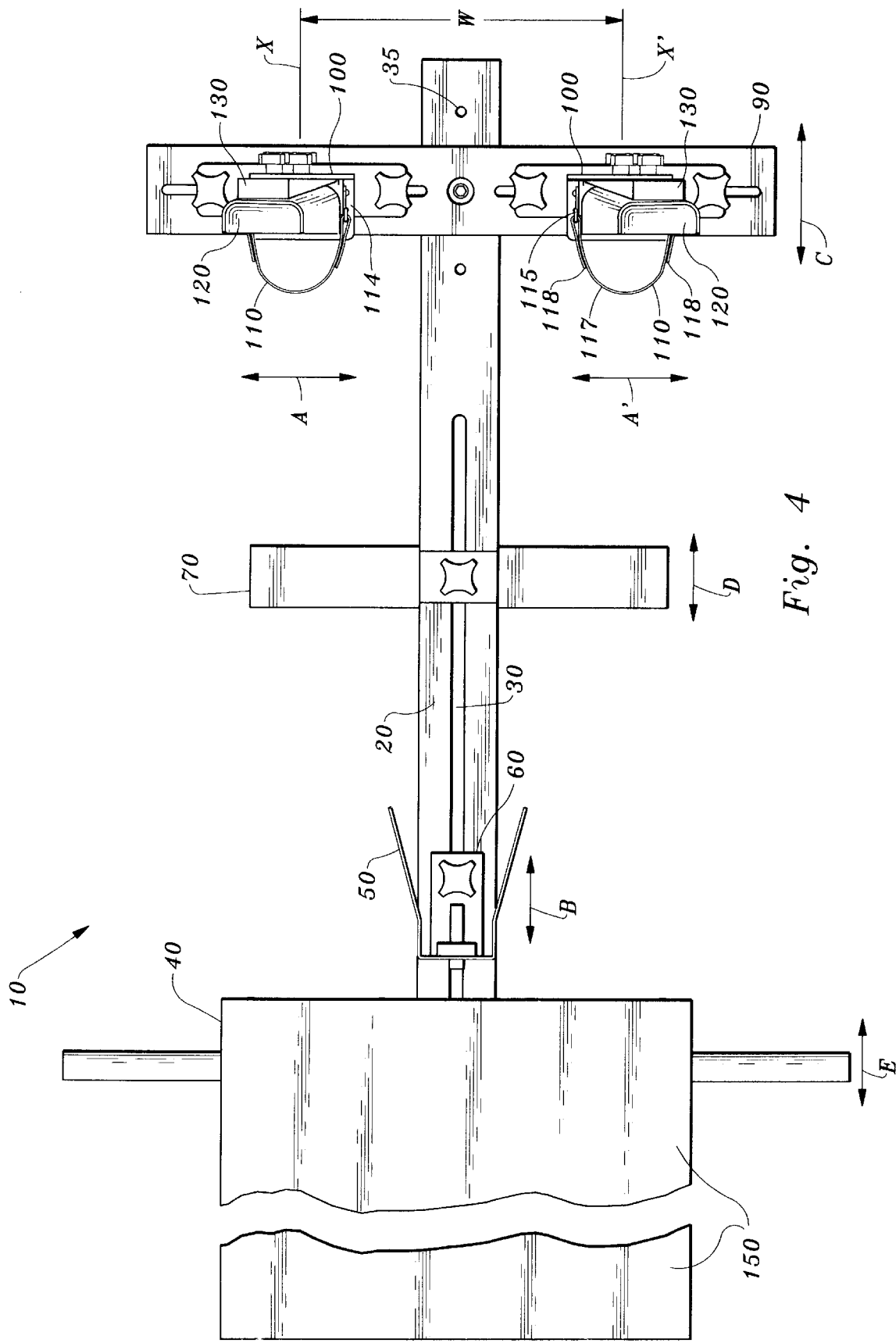
FIG. 4 is a top plan view of that which is shown in FIG. 3.

More specifically, and with particular reference to FIGS. 2–4, details of the center frame rail 20 are provided. The center frame rail 20 is an elongate rigid linear construct formed from a high strength material such as aluminum. The center frame rail 20 is preferably an orthorhombic parallelepiped having a constant thickness, constant width and constant length (preferably approximately 1 meter). Thus, the center frame rail 20 features a parallel rectangular top 22 parallel to a parallel rectangular bottom 24. Two parallel sides 25 extend between the top 22 and the bottom 24. An upper end 26 and lower end 28 also extend between the top 22 and the bottom 24. A long axis of the overall casting device 10 is generally defined by a line running perpendicular to the upper end 26 and the lower end 28 and passing through a center of the center frame rail 20 along its length, oriented parallel to and between the foot positioning support 100 width axes X, X'. A vertical plane passing through this long axis of the casting device 10 is generally referred to as a central plane for the casting device 10.

A slit 30 passes through the center frame rail 20 from the top 22 down to the bottom 24. This slit 30 does not extend all the way from the upper end 26 to the lower end 28. Rather, the slit 30 extends from a region near the upper end 26 to a region near a mid point between the upper end 26 and the lower end 28, but extending slightly beyond the midpoint and toward the lower end 28. Approximately two-thirds of the overall length of the center frame rail 20 has the slit 30 passing there through. Preferably, three lower threaded holes 35 pass from the top surface 22 down to the bottom surface 24 between where the slit 30 terminates and the lower end 28 of the center frame rail 20. As discussed below, the slit 30 allows various different components of the casting device 10 to be coupled to the center frame rail 20 at continuously variable locations along the slit 30. The lower threaded holes 35 provide three different distinct positions for the stance width section 90 of the casting device 10.

With particular reference to FIG. 2, details of the gluteal support section 40 are provided. The gluteal support section 40 is essentially a hollow rigid construct which is generally configured as a tetragonal parallelepiped. The gluteal support section 40 includes a planar top wall 42 oriented substantially horizontally and spaced from a bottom wall 44 parallel thereto. The top wall 42 provides a planar horizontal surface for support of central portions of the patient P. The top wall 42 has a circular opening 43 passing there through which facilitates attachment and position adjustment of the gluteal support section 40 with respect to the center frame rail 20.

The bottom wall 44 features feet 45 adjacent lateral ends of the gluteal support section 40. The feet 45 ensure that the gluteal support section 40 will have solid contact with the surface upon which the casting device 10 is oriented, even if the underlying support surface is not entirely planar. A central slot 46 extends up into the bottom wall 44 somewhat, providing clearance for the center frame rail 20 to rest under the gluteal support section 40 while not displacing the feet 45 of the gluteal support section 40 off of the support surface.

A handlebar 48 of generally cylindrical elongate form passes through the hollow interior of the gluteal support section 40 and extends out of lateral sides of the gluteal support section 40. The handlebar 48 has a diameter which allows it to be easily grasped by hands H of the patient P. The handlebar 48 provides additional comfort to the patient P and allows the patients to more easily position themselves upon the casting device 10. The handlebar 48 can either be removably attachable to the gluteal support section 40 or can be permanently attached to the gluteal support section 40 as by welding.

The gluteal support section 40 is attached to the center frame rail 20 through a gluteal support bolt 49 which passes through the bottom wall 44 of the gluteal support section 40, through an appropriately sized hole, and is then threaded into a gluteal support T-nut 41 oriented below the slit 30 in the center frame rail 20. Details of the gluteal support T-nut 41 are provided below. By screwing the gluteal support bolt 49 into the gluteal support T-nut 41, the gluteal support section 40 is caused to be securely attached to and slidably supported by the center frame rail 20.

With particular reference to FIGS. 2–5, details of the sub-perineal spacer 50 and sub-perineal carrier 60 are provided. The sub-perineal spacer 50 is a rigid irregularly shaped construct which is configured to provide optimal spacing between the legs L of the patient P (FIG. 1) during casting of lower extremities of the patient P. Particularly, the sub-perineal spacer 50 ensures that at least a minimum width is maintained between the legs L of the patient P for an orthotic device to be made from the casts taken. This minimum width provides the necessary clearance in the sub-perineal region for the orthotic device to function properly.

The sub-perineal spacer 50 includes a planar vertical upper wall 52 which is oriented generally perpendicular to the long axis of the casting device 10. The upper wall 52 can have different widths depending on the particular needs of the patient P. For instance, a child's sub-perineal spacer 50 would have an upper wall 52 of preferably 51 millimeters. An adult's sub-perineal spacer 50 would have an upper wall 52 of preferably 65 millimeters. An extra large sub-perineal spacer 50 would have an upper wall 52 of preferably 74 millimeters. Two side flanges 54 extend from lateral edges of the upper wall 52 in a direction away from the gluteal support section 40 and toward the stance width section 90. The side flanges 54 are not completely planar. Rather, the side flanges 54 include a parallel region 55 where the two opposite side flanges 54 are parallel to each other and perpendicular to the upper wall 52, and a divergent region 56 where the side flanges 54 are skewed with respect to the upper wall 52 and with respect to each other. Both the parallel region 55 and divergent region 56 of the side flanges 54 remain perpendicular to a leg L plane which is perpendicular to the center plane and oriented essentially horizontally when the casting device 10 is oriented upon a horizontal surface.

The divergent regions 56 of the sub-perineal spacer 50 diverge away from each other as they extend away from the upper wall 52 toward their tips 57. The divergent regions 56 diverge at an angle of between 5° and 15° from the central plane, but preferably diverge only 7.5° from the central plane and hence 15° from each other. The subperineal spacer 50 includes top edges 58 and bottom edges 59 which are generally aligned in horizontal planes parallel to each other. The top edges 58 are sufficiently elevated above the bottom edges 59 that they cause the legs L of the patient P to go around the sub-perineal spacer 50 rather than over the top of the sub-perineal spacer 50. The bottom edges 59 of the sub-perineal spacer 50 are generally adjacent the top 22 of the center frame rail 20.

The sub-perineal spacer 50 is not directly coupled to the center frame rail 20. Rather, the sub-perineal spacer 50 couples to the sub-perineal carrier 60 through a spacer bolt 51. This spacer bolt 51 passes through the upper wall 52 and threads into the vertical leg 61 of the sub-perineal carrier 60. The sub-perineal carrier 60 includes the vertical leg 61 extending vertically upward from a horizontal leg 66 with a gusset 62 oriented diagonally between the vertical leg 61 and the horizontal leg 66. The vertical leg 61 includes a spacer bolt hole 63 near a free end 64 thereof which receives the spacer bolt 51 for attachment of the sub-perineal spacer 50 to the vertical leg 61 of the sub-perineal carrier 60. The vertical leg 61 extends from the free end 64 down to a base end 65 adjacent the horizontal leg 66. The vertical leg 61 is attached to the horizontal leg 66 such as by welding the base end 65 of the vertical leg 61 to the horizontal leg 66.

The horizontal leg 66 includes a top end 67 directly adjacent the base end 65 of the vertical leg 61 and a bottom end 68 which extends away from the top end 67 in a direction heading toward the stance width section 90 and away from the sub-perineal spacer 50. Both the vertical leg 61 and horizontal leg 66 are preferably rigid planar constructs which are oriented perpendicular to each other. The carrier 60 thus provides one means to adjustably secure and position and slidably attach the sub-perineal spacer 50 with respect to other parts of the casting device 10.

With particular reference to FIG. 2, details of the knee support section 70 are provided. The knee support section 70 is an elongate rigid construct oriented generally perpendicular to the long axis of the casting device 10. The knee support section 70 is adjustably attached to the central frame rail 20 along the slit 30. The knee support section 70 includes two horizontal support surfaces 72, one on each side of the central frame rail 20, at positions which would generally provide the support surfaces 72 of the knee support section 70 beneath the knees of the patient P (FIG. 1). The knee support section 70 includes a planar horizontal bar 74 which is oriented perpendicular to the center frame rail 20 and has the support surfaces 72 extending up from the bar 74. Preferably, the support surfaces 72 are supported sufficiently above the bar 74 that a hollow space is provided between the support surfaces 72 and the bar 74, to decrease a weight added to the casting device 10 by the knee support section 70.

A center of the bar 74 includes a knee support bolt hole 75 passing vertically there through. A large cap support bolt 76 is provided which is sized to pass through the knee support bolt hole 75 and then to thread into a knee support T-nut 79 oriented below the slit 30 in the center frame rail 20 with the large cap support bolt 76 passing through the slit 30. Additionally, a washer 78 is preferably interposed between the large cap support bolt 76 and a bolt head 77 of the large cap support bolt 76. Preferably, the bolt head 77 is configured to be large enough to be grasped by a hand of an orthotist or other user of the casting device 10. Additionally, the bolt head 77 preferably includes tactile enhancement such as knobs or other protuberances to make the large cap support bolt 76 more easily rotated by hand.

Preferably, a large cap support bolt 76 is also provided along with a washer 78 passing through the horizontal leg 66 of the sub-perineal carrier 60 for attachment of the sub-perineal carrier 60 and sub-perineal spacer 50 in an adjustable fashion to the slit 30 of the center frame rail 20. A sub-perineal carrier T-nut 69 is provided beneath the slit 30 of the center frame rail 20 to complete the adjustable attachment of the sub-perineal carrier 60 and sub-perineal spacer 50 to the center frame rail 20.

With particular reference to FIG. 2, details of the gluteal support T-nut 41, carrier T-nut 69 and knee support T-nut 79 are provided. Preferably, each T-nut 41, 69, 79 is of an identical construction. Each T-nut 41, 69, 79 includes an upper narrow portion 82 which has a width similar to but not greater than a width of the slit 30. Thus, the upper narrow portion 82 can pass into the slit 30 from beneath the center frame rail 20. Each T-nut 41, 69, 79 preferably includes a lower wide portion 84 which has a width greater than the width of the slit 30. Thus, each T-nut 41, 69, 79 can pass up into the slit 30 partway with the narrow upper portion 82 nested within the slit 30, but not all the way through the slit 30, because the lower wide portion 84 impacts the center frame rail 20 adjacent sides of the slit 30. Each T-nut 41, 69, 79 is preferably provided with a length 86 which is greater than a width of the slit 30. Thus, both the upper narrow portion 82 of the T-nuts 41, 69, 79 are prevented from rotating once the upper narrow portion 82 is nested within the slit 30. In this way, the T-nuts 41, 69, 79 are prevented from rotating when the large cap support bolts 76 or the gluteal support bolt 49 are rotated. Each T-nut 41, 69, 79 includes a threaded bore 88 passing through the upper narrow portion 82 and the lower wide portion 84. The threaded bore 88 is sized with a similar diameter and thread pitch to that exhibited by the large cap support bolts 76 and the gluteal support bolt 49.

With particular reference to FIGS. 2–4, details of the stance width section 90 and related attached structures are provided. The stance width section 90 has a similar configuration to that of the gluteal support section 40. Thus, the stance width section 90 is an elongate rigid construct of generally orthorhombic parallelepiped configuration. A bottom plate 96 of the stance width section 90 supports feet 97 thereon similar to the feet 45 of the gluteal support section 40. The feet 97 are oriented adjacent lateral extremities of the stance width section 90 and provide stability to the casting device 10 along with the feet 45 of the gluteal support section 40. A center slot 98 in the bottom plate 96 is configured similarly to the central slot 46 of the gluteal support section 40 to provide clearance for the center frame rail 20 beneath the bottom plate 96 of the stance width section 90.

The stance width section 90 includes a horizontal planar top plate 91 which has two lateral slits 92 oriented thereon which are co-linear with each other and oriented perpendicular to the long axis and central plane of the casting device 10. Each lateral slit 92 extends from a location slightly spaced from a center of the top plate 91 out to a region just short of the lateral extremities of the stance width section 90. An opening 93 passes through the top plate 91 at a geometric center of the top plate 91. The lateral slits 92 and the opening 93 extend entirely from an upper surface 94 of the top plate 91 through to a lower surface 95 of the top plate 91.

The opening 93 allows a stance width bolt 99 to pass through the top plate 91 and down to the bottom plate 96 where it can pass through the bottom plate 96 and be threaded into the lower threaded holes 35 of the center frame rail 20. The head of the stance width bolt 99 is sized sufficiently large to compress the bottom plate 96 of the stance width section 90 against the center frame rail 20 and secure the stance width section 90 adjacent the center frame rail 20. Three different lower threaded holes 35 are provided in the center frame rail 20 to provide three different alternative locations for the stance width section 90 along the center frame rail 20.

Each lateral slit 92 is provided to allow one of two foot positioning supports 100 to be secured to the top plate 91 of the stance width section 90. Each of the two foot positioning supports 100 is identical to the other foot positioning support 100 except that they are mirror images of each other so that one foot positioning support 100 is particularly configured for use with a left foot F of the patient P and the other foot positioning support 100 is particularly configured for the right foot F of the patient P. For convenience, the foot positioning supports 100 and associated structures will be discussed together. Each foot positioning support 100 includes a horizontal planar base 102 having a forward edge 101 parallel to and spaced from a rear edge 103. The base 102 is configured to rest upon the upper surface 94 of the top plate 91 of the stance width section 90. A riser 104 extends vertically up from the base 102. Preferably, the riser 104 is secured to the base 102 such as by welding. Both the base 102 and riser 104 are preferably formed from rigid material such as stainless steel so that when the base 102 is resting upon the top plate 91 of the stance width section 90, the riser 104 is maintained in a precisely vertical orientation perpendicular to the long axis of the casting device 10.

Each riser 104 includes a lower edge 105 adjacent the base 102 and an upper edge 106 opposite the lower edge 105. The riser 104 includes a tapered inner side 107 extending from the lower edge 105 to the upper edge 106 and a tapered outer side 108 extending from the lower edge 105 to the upper edge 106. The inner tapered side 107 and tapered outer side 108 are not parallel to each other. Rather, the sides 107, 108 are closer to each other adjacent the upper edge 106 than they are adjacent the lower edge 105.

A riser slit 109 passes through the riser 105 and is oriented parallel to the tapered inner side 107 of each riser 104. Preferably the tapered outer side 108 is oriented vertically and the tapered inner side 107 is skewed with respect to the vertical. Because the riser slits 109 of each foot positioning support 100 are oriented parallel to the tapered inner side 107 along a foot axis Z' (FIG. 3), the two riser slits 109 extend away from each other as they extend vertically upward. This angle by which the riser slits 109 diverge from a vertical orientation is referred to as the toe out angle α (FIGS. 1 and 3).

The toe out angle α preferably measures between 2.50° and 7.5° so that a total angular divergence of the two riser slits 109 from each other is between 5° and 15°. This toe out angle α is provided particularly for taking casts of lower extremities of a patient P in the preparation of orthotic devices such as the "Up & About" orthotic device. If other orthotic devices are to be created through the use of this casting device, different toe out angles α could be utilized ranging from 0° to 15°. The toe out angle α can also be made adjustable for precise selection of a specific desired toe out angle α by the orthotist.

Each foot positioning support 100 includes an ankle restraint strap 110 which extends from the foot positioning supports 100 in a position allowing the ankle restraint straps 110 to hold ankles of the patient P adjacent the foot positioning supports 100 when the casting device 10 is in use. Two gussets 111 are provided for each foot positioning support 100. Each gusset 111 is oriented vertically in a plane perpendicular to the plane including the riser 104 and perpendicular to the plane including the base 102. The gussets 111 not only support the riser 104 in its vertical position, but also provide for attachment of gusset pins 113 to which fixed strap rings 114 and free strap rings 115 can be attached for support of the ankle restraint straps 110.

Each ankle restrain strap 110 includes ends 118 which can be threaded through the fixed strap ring 114 and the free strap ring 115. Preferably, the outer surface 117 of each ankle support strap 110 is provided simultaneously with both different types of velcro material which can attach to each other. Thus, the ends 118 of the ankle restraint straps 110 can be looped through the rings 114, 115 and then have the outer surface 117 doubled back upon itself with different complemental surfaces of velcro, or other attachment means on the outer surfaces 117, connected together. Preferably, the fixed strap ring 114 is configured such that the ankle restraint strap 110 can not be adjusted on that end, but with the free strap ring 115 free to allow the ankle restrain straps 110 to pass through, adjusting the length of the ankle restrain straps 110. Alternatively, both of the rings 114, 115 can be free to allow for adjustment of the ankle restraint straps 110I A foot shell 120 is provided adjacent each foot positioning support 100 on a side of each foot positioning support 100 facing the sub-perineal spacer 50 and gluteal support section 40. Each foot shell 120 is particularly configured to conform generally to the contour of the foot F of the patient P to be supported therein. Thus, a left foot shell 120 is provided adjacent the left foot positioning support 100 and a right foot shell 120 is provided adjacent the right foot positioning support 100. The left and right foot shells 120 are mirror images of each other. To accommodate different foot F sizes, foot shells 120 having different sizes can be utilized.

Each foot shell 120 includes a sole plate 122 which is generally planar. Support holes 123 pass through the sole plate 122 preferably near a toe end of the foot shell 120 and near a heel end of the foot shell 120. Shell bolts 124 are sized to pass through the support holes 123 and through the riser slits 109. Shell nuts 125 are provided which can thread onto the shell bolts 124 to tighten the foot shells 120 in position along the riser slits 109. Because the foot shells 120 are secured to the foot positioning supports 100 through the riser slits 109, not only can minor elevational adjustments to the position of the feet F of the patient P be provided for, but also the riser slit 109 and shell bolts 124 accommodate modification of a dorsiflexion angle β discussed below.

Each foot shell 120 additionally includes a heel wall 126 which is generally perpendicular to the sole plate 122 and side walls 128 which extend from the heel wall 126 on each side of the sole plate 122 and also generally perpendicular from the sole plate 122. The walls 126, 128 provide one means to restrict foot F rotation. Preferably, the end of the sole plate 122 adjacent toes of the patient P are open to accommodate patients P having feet F of different sizes.

Figure 5:
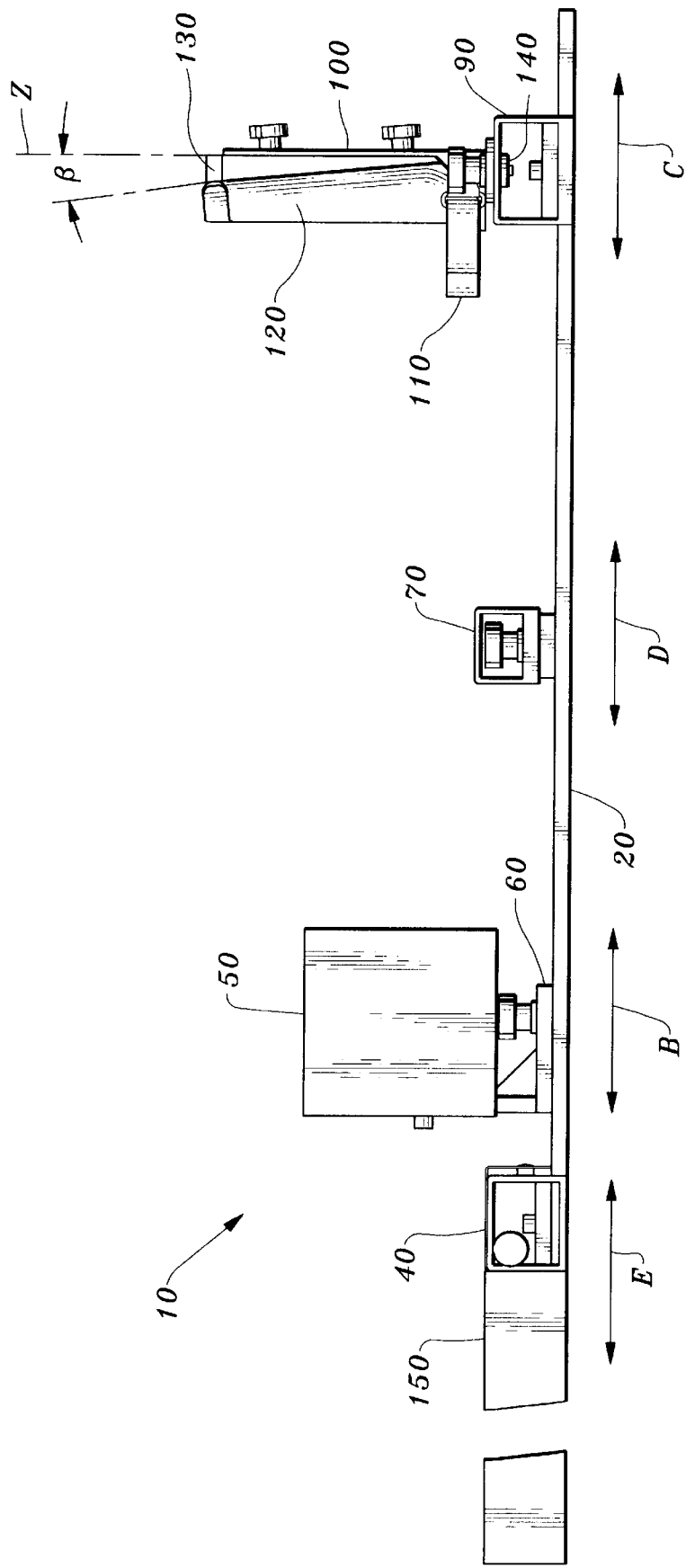
FIG. 5 is a side elevation view of that which is shown in FIG. 3.

An important feature of the casting device 10 is its ability to accommodate dorsiflexion angles β having different measurements (FIGS. 1 and 5). Of particular importance is the accommodation of negative dorsiflexion angles β which cause toes of the patient P to be closer to the head of the patient P than heels of the patient P, during the casting process. To create this negative dorsiflexion angle β, away from a vertical heel plane perpendicular to the central plane, dorsiflexion wedges 130 are provided. Each dorsiflexion wedge 130 is generally a rigid construct having a triangular cross section such that each wedge 130 has a thin end 132 and a thick end 134. A central channel 135 passes through this thin end 132 and extends up toward the thick end 134. Each wedge 130 features two surfaces which are not quite parallel to each other but rather taper toward each other from the thick end 134 to the thin end 132 where the two surfaces meet. These surfaces include a shell surface 136 and a riser surface 138.

Each dorsiflexion wedge 130 is positioned between one of the foot positioning supports 100 and the adjacent foot shell 120 with the shell bolts 124 passing through the central channel 135 in the dorsiflexion wedge 130. The thick end 134 of the dorsiflexion wedge 130 is oriented above the thin end 132 of the dorsiflexion wedge 130. Each dorsiflexion wedge 130 is thus free to slide downward along the shell bolts 124 and along the central channel 135 of the dorsiflexion wedge 130. The further the dorsiflexion wedge 130 is lowered into position between each foot positioning support 100 and each foot shell 120, the greater the dorsiflexion angle β which results.

If the dorsiflexion wedge 130 is only slightly inserted between the foot positioning support 100 and foot shell 120, the dorsiflexion angle β would measure approximately 0°, but slightly greater than 0°. As the dorsiflexion wedge 130 is lowered further down, the dorsiflexion angle increases. Preferably, the dorsiflexion angle β does not exceed 10° when the dorsiflexion wedge 130 is lowered down as far as possible between the foot positioning support 100 and foot shell 120. Depending on the needs of the patient P and the judgment exercised by the orthotist, different dorsiflexion angles β, can be selected, typically between 2° and 4°. Once this dorsiflexion angle β is set, and the feet F of the patient P are secured within the foot shells 120, the casting device 10 can be utilized to form casts of the patient P which exhibit an optimal dorsiflexion angle β. The dorsiflexion wedges 130 thus provide one means to adjust the dorsiflexion angle β.

A foot positioning bracket 140 is oriented beneath each top plate 91 in the stance width section 90 which is attachable to the base 102 of each foot positioning support 100. Each foot positioning bracket 140 is preferably a rigid elongate construct which has bracket ends 142 with threaded holes 144 adjacent each bracket end 142. The base 102 of each foot positioning support 100 includes two side holes 146 passing there through. These side holes 146 are spaced apart a similar distance as are the threaded holes 144 of the foot positioning brackets 140.

Bracket bolts 148 are provided which pass through the side holes 146, through the lateral slits 92 and into the threaded holes 144 of the foot positioning brackets 140. When these bracket bolts 148 are loose, a stance width W (FIG. 4) between the two foot positioning supports 100 can be adjusted. Two axes X, X' are aligned with the heel location of each foot positioning support 100, defining the adjustable stance width W. If desired, indicia can be placed on the upper surface 94 to indicate the selected stance width W. Once the stance width W is provided as desired, the bracket bolts 148 can be tightened to fix the foot positioning supports 100 in position with respect to the stance width section 90. Preferably, the bracket bolts 148 have heads similar to the large cap support bolts 76 so that they can be easily rotated by hand.

With reference to FIG. 2, details of the pad 150 are provided. The pad 150 is generally a rectangular resilient structure of constant thickness between a top surface 152 and a bottom surface 153. The top surface 152 includes an overhanging shroud 154 of flexible material extending from one end thereof a sufficient distance to allow the overhanging shroud 154 to be draped over the gluteal support section 40. The overhanging shroud 154 includes snaps 155 thereon which are complemental to snaps 156 on a lower wall 158 of the gluteal support section 40. When the snaps 155 are secured with the snaps 156, the pad 150 and overhanging shroud 154 are securely attached to the gluteal support section 40 and provide a horizontal surface which the patient P can rest upon in comfort. A core 157 of the pad 150 is preferably filled with a resilient material such as an open celled polyurethane foam. Preferably the core 157 is surrounded by a layer of vinyl or other fabric which can be easily washed.

With particular reference to FIG. 1, details of the operation of the casting device 10 are provided. Initially, the casting device 10 is constructed from an unassembled position by first laying the center frame rail 20 upon a horizontal flat surface and then laying the gluteal support section 40, sub-perineal spacer 50 and sub-perineal carrier 60, knee support section 70, and stance width section 90 over the center frame rail 20. The gluteal support section 40 is attached to the slit 30 of the center frame rail 20 through use of the gluteal support bolt 49 and gluteal support T-nut 41. The sub-perineal spacer 50 and sub-perineal carrier 60 are attached to the slit 30 of the center frame rail 20 through one of the support bolts 76 and the carrier T-nut 69. The knee support section 70 is attached to the slit 30 of the center frame rail 20 through one of the large cap support bolts 76 and the knee support T-nut 79. The stance width section 90 is attached to the center frame rail 20 through one of the lower threaded holes 35.

The orthotist then takes the pad 150 and orients it adjacent the gluteal support section 40 with the top surface 152 facing upwards and with the overhanging shroud 154 stretching over the top wall 42 of the gluteal support section 40 and adjacent the lower wall 158 of the gluteal support section, where the overhanging shroud 154 is attached to the gluteal support section 40 through the snaps 155, 156.

The orthotist then makes careful measurements of the patient P to make further adjustments to the casting device 10. Of particular interest is the full length of the patient P from the patient's perineum to the patient's feet F. Also, a distance from the knee of the patient P to the foot F should be provided. These measurements are then used to adequately position the stance width section 90 in the appropriate lower threaded holes 35 (arrow C of FIG. 4), locate the knee support section 70 (arrow D of FIG. 4), the sub-perineal spacer 50 (arrow B of FIG. 4) and the gluteal support section 40 (arrow E of FIG. 4).

Specifically, the knee support section 70 is oriented, along arrow D, a distance away from the stance width section 90 which matches a length from the knee of the patient P to the foot F of the patient P. The gluteal support section 40 is located, along arrow E, a distance away from the stance width section 90 similar to but slightly greater than a full length from the perineum of the patient P to the foot F of the patient P. Finally, the perineal spacer 50 is slid along the slit 30, along arrow B, through the sub-perineal carrier 60 until the sub-perineal spacer 50 is oriented between 10 and 30 millimeters from the perineum of the patient P.

Once these various components of the casting device 10 are located and secured in position, the stance width W of the foot positioning supports 100 can then be adjusted (along arrow A, A' of FIG. 4) to match the height of the patient P. For instance, if the patient P has a height between 5' and 5'6", the stance width W should be between 22 and 23 centimeters. If the patient P has a height between 5'6" and 5'10" the stance width should be between 23 centimeters and 24.5 centimeters. If the patient has a height greater than 5'11" inches, the stance width can be further increased to correspond to the needs of the patient P.

Before the patient P is placed upon the casting device 10, the dorsiflexion wedges 130 are inserted between the foot shells 120 and foot positioning supports 100 to the desired depth to provide the desired dorsiflexion angle β. Preferably, the dorsiflexion angle measures between 2° and 4°. For convenience in picking the appropriate dorsiflexion angle β, indicia can be located upon the dorsiflexion wedges 130 and upon the foot shells 120 and foot positioning supports 100 to allow the orthotist to clearly identify when the dorsiflexion wedges 130 are appropriately positioned to provide the desired dorsiflexion angle β.

The patient P is then placed upon the casting device 10 with the torso and head of the patient P resting upon the pad 150 and with the lower extremities of the patient P extending from the gluteal support section 40, around the sub-perineal spacer 50, over the knee support section 70 and down to the stance width section 90 where the feet F of the patient P are secured within the foot shells 120 using the ankle restraint straps 110.

Appropriate casting materials are applied to the lower extremities of the patient P depending on the type of casting process to be utilized and according to the known techniques for applying different casting materials. Once the casting materials have been applied, but before they have hardened, the position of the lower extremities of the patient P are finally checked and the ankle restraint straps 110 are tightened to ensure that the feet F of the patient P are firmly adjacent the foot shells 120 of the foot positioning supports 100.

The casting material is then allowed to harden with the patient P resting comfortably upon the casting device 10. Once the casting material has hardened, known techniques can be utilized for removal of the casting material and for further steps necessary to utilize the cast taken of the lower extremities of the patient P for the desired purposes. The patient P is removed from the casting device 10 and the various different components of the casting device 10 can be cleaned and then prepared for reuse or collapsed for storage or transport.

Moreover, having thus described the preferred embodiment of this invention, it should be apparent that various different embodiments and modifications to this invention could be resorted to while remaining within the scope of this invention. For instance, while specific structures are disclosed for restraining the lower extremities of the patient P in the desired position, the structures could be altered in shape, size and appearance while maintaining their underlying individual extremity positioning and restraining functions. Additionally, while the casting device 10 of this preferred embodiment is particularly configured for formation of casts for use in the optimal sizing and construction of custom manufactured orthotic devices such as those utilized by paraplegics, with slight modifications to the casting device 10, casts for other orthotic devices and for other purposes could be effectively accommodated.

What is claimed is:

1. A casting apparatus for positioning and supporting lower extremities of a person during casting of the lower extremities, the casting apparatus comprising in combination:

a pair of foot positioning supports, each foot positioning support including a sole plate;

said sole plate having a toe end and a heel end;

said toe end of said sole plate configured to be closer to the person's head when the person is lying flat and has feet adjacent said foot positioning supports than said heel end of said sole plate; and wherein a rigid elongate center frame rail is provided between the person's legs when the person lying flat has feet adjacent said foot positioning supports, said central frame rail including means to adjustable secure said foot positioning supports to said center frame rail.

2. The casting apparatus of claim 1 wherein each said foot positioning support is oriented to cause said toe ends of each said sole plate to be spaced further apart than said heel ends of each said sole plate, such that a toe out angle is provided between said sole plates measuring between 0° and 30°.

3. The casting apparatus of claim 2 wherein said casting apparatus includes a means to adjust a dorsiflexion angle defined by an amount that said toe ends of each said sole plate diverge from a position directly above said heel ends of each said sole plate, such that said dorsiflexion angle can be securely fixed at one angle and then later adjusted to be securely fixed at a second new angle.

4. The casting apparatus of claim 3 wherein said sub-perineal spacer is provided having a lateral width between side flanges thereof of at least 50 millimeters, said sub-perineal spacer including a means to be adjustably positioned and secured to said center frame rail at different distances away from said foot positioning supports, such that said sub-perineal spacer can be located in a fixed position between the person's legs and between 10 millimeters and 30 millimeters from the person's perineum.

5. The casting apparatus of claim 4 wherein each said foot positioning support is coupled to a single stance width section, said stance width section including a means to adjust a distance between each said foot positioning support, such that a distance between said foot positioning supports can be adjusted.

6. A casting apparatus for positioning and supporting lower extremities of a person during casting of the lower extremities, the casting apparatus comprising in combination:

a pair of foot positioning supports, each foot positioning support including a sole plate;

said sole plate having a toe end and a heel end;

said toe end of said sole plate configured to be closer to the person's head when the person is lying flat and the person's feet are adjacent said foot positioning supports than said heel end of said sole plate;

wherein said casting apparatus includes means to hold the sole of the person's foot adjacent said sole plates;

wherein each said foot positioning support is oriented to cause said toe ends of each said sole plate to be spaced further apart than said heel ends of each said sole plate, such that a toe out angle is provided between said sole plates measuring between 0° and 30°;

wherein said casting apparatus includes a means to adjust a dorsiflexion angle defined by an amount that said toe ends of each said sole plate diverge from a position directly above said heel ends of each said sole plate, such that said dorsiflexion angle can be securely fixed at one angle and then later adjusted to be securely fixed at a second new angle;

wherein a sub-perineal spacer is provided having a lateral width between side flanges thereof of at least 50 millimeters, said sub-perineal spacer including a means to be adjustable positioned and secured at different distances away from said foot positioning supports, such that said sub-perineal spacer is configured to be located in a fixed position between the person's legs and between 10 millimeters and 30 millimeters from the person's perineum;

wherein each said foot positioning support is coupled to a single stance width section, said stance width section including a means to adjust a distance between each said foot positioning support, such that a distance between said foot positioning supports can be adjusted; and wherein a rigid elongate linear center frame rail is configured to be between the person's legs when the person is lying flat and the person's feet are adjacent said foot positioning supports, said central frame rail including means to adjustably secure said stance width section to said center frame rail and means to adjustably secure said sub-perineal spacer to said central frame rail, such that a distance between said foot positioning supports on said stance width sections can be secured with respect to the position of said sub-perineal spacer.

7. The casting apparatus of claim 6 wherein a slit is oriented passing through said center frame rail, said slit being linear with a long axis parallel to said center frame rail, said means to adjustably secure said sub-perineal spacer to said center frame rail including a sub-perineal carrier including means to slide linearly along said slit and means to be attached and detached from said center frame rail while remaining oriented partially within said slit of said center frame rail, for sliding along said slit.

8. The casting apparatus of claim 7 wherein a gluteal support means is provided, said gluteal support means including a means to slide along said slit of said center frame rail and be secured to said center frame rail, said gluteal support means including a substantially horizontal top wall, said gluteal support means including an upper torso pad attached thereto, said upper torso pad including a core of resilient material, said gluteal support means including handles extending from lateral ends thereof, said handles configured to be grasped by hands of a person while resting upon said pad and with the person's feet held to said foot positioning supports of said casting apparatus.

9. The casting apparatus of claim 7 wherein a knee support means is provided, said knee support means including a means to slidably attach to said center frame rail through said slit, said knee support means oriented between said sub-perineal spacer and said stance width section, said knee support means having a support surface oriented parallel to said leg plane, said support surface having sufficient width to underlie a back side of the person's legs adjacent the person's knees when the person is resting upon said casting apparatus with the person's feet secured to said foot positioning supports.

10. The casting apparatus of claim 6 wherein said sub-perineal spacer includes said side flanges having a parallel region and a divergent region, said divergent region closer to said stance width section of said casting apparatus than is said parallel region, said divergent region of each said side flange oriented at an angle diverging from said center frame rail measuring between 0° and 15°, said divergent regions of each side flange of said sub-perineal spacer diverging at a common angle from said central frame rail.

11. The casting apparatus of claim 6 wherein said means to hold the sole of the person's foot adjacent said sole plates includes a strap fixed to said foot positioning supports through strap rings adjacent sides of said foot positioning supports, said straps having adjustable length for securing of the foot to said sole plates adjacent said foot positioning supports; and wherein said casting apparatus includes means to hold the sole of the person's foot adjacent said sole plates.

12. A casting apparatus for positioning and supporting lower extremities of a person during casting of the lower extremities, the casting device comprising in combination:

a pair of foot positioning supports, each foot positioning support including a sole plate;

said sole plate having a toe end and a heel end;

said toe end of said sole plate is configured to be closer to the person's head when the person is lying flat and has feet adjacent said foot position supports than said heel end of said sole plate;

wherein said casting apparatus includes means to hold the sole of the person's foot adjacent said sole plates;

wherein each said foot positioning support is oriented to cause said toe ends of each said sole plate to be spaced further apart than said heel ends of each said sole plate, such that a toe out angle is provided between said sole plates measuring between 0° and 30°;

wherein said casting apparatus includes a means to adjust a dorsiflexion angle defined by an amount that said toe ends of each said sole plate diverge from a position directly above said heel ends of each said sole plate, such that said dorsiflexion angle can be securely fixed at one angle and then later adjusted to be securely fixed at a second new angle; and wherein said means to adjust said dorsiflexion angle includes a wedge having a thin end oriented below a thick end, said dorsiflexion wedge oriented between said sole plate and said foot positioning support, said wedge including means to be slidably positioned at various different positions to alter said dorsiflexion angle.

13. A casting device for positioning and supporting lower extremities of a person during casting of the lower extremities, the casting device comprising in combination:

a pair of foot positioning supports, each foot positioning support including a sole plate;

said sole plate having a toe end, and a heel end;

means to restrict rotation of the person's feet while the person's feet are adjacent said sole plates;

wherein said toe end of said sole plate is configured to be closer to the patient's head than said heel end of said sole plate when the person is oriented with the person's feet adjacent said sole plates of said casting device;

wherein said casting device includes a rigid elongate linear central frame rail, said frame rail having a stance width section supported upon an upper surface thereof adjacent a lower end thereof, said stance width section having a pair of lateral slits oriented perpendicular to a long axis of said center frame rail, each said foot positioning support slidably secured to said stance width section through bolts passing through said slits in said stance width section;

said casting device including a sub-perineal spacer having a width configured to be at least as great as a minimum width between legs of the person at a distance between 10 millimeters and 30 millimeters from the person's perineum, said sub-perineal spacer including means to slidably attach to said center frame rail and configured to be at a position between 10 millimeters and 30 millimeters from the person's perineum when the person is lying flat and the person's feet are adjacent said foot positioning supports; and wherein said casting device includes a gluteal support section slidably secured to said center frame rail through a slidable support means, said gluteal support section including a substantially horizontal top wall, said gluteal support section including a torso pad removably attachable thereto and extending away from said gluteal support section in a direction away from said stance width section of said casting device, said pad oriented substantially horizontal and sized at least as large as a torso of the person, said foot psitioning supports including straps attached thereto having sufficient length and adjustability to secure the feet of the person adjacent said sole plates.

14. A casting apparatus for positioning and supporting lower extremities of a person during casting of the lower extremities, the casting apparatus comprising in combination:

a pair of foot positioning supports, each foot positioning support including a sole plate;

said sole plate having a toe end and a heel end;

said toe end of said sole plate configured to be closer to the person's head when the person is lying flat and has feet adjacent said foot positioning supports than said heel end of-said sole plate;

wherein said casting apparatus includes a means to adjust a dorsiflexion angle defined by an amount that said toe ends of each said sole plate diverge from a position directly above said heel ends of each said sole plate, such that said dorsiflexion angle can be securely fixed at one angle and then later adjusted to be securely fixed at a second new angle; and wherein said means to adjust said dorsiflexion angle includes a wedge having a thin end oriented below a thick end, said dorsiflexion wedge oriented between said sole plate and said foot positioning support, said wedge including means to be slidably positioned at various different positions to alter said dorsiflexion angle.

15. A casting apparatus for positioning and supporting lower extremities of a person during casting of the lower extremities, the casting apparatus comprising in combination:

an elongate center rail positionable substantially horizontally;

a sub-perineal spacer attached to said center rail and extending up from said center rail, said sub-perineal spacer sized to fit between legs of a person when said center rail is oriented to extend horizontally between the person's legs and the person is lying horizontally;

two foot positioning supports, each foot positioning support including a sole plate, each said sole plate having a toe end and a heel end, said toe end of each said sole plate configured to be closer to the person's head when the person is lying flat and the person's feet are adjacent said foot positioning supports than said-heel end of said sole plates, said foot positioning supports attached to said center rail.

16. The apparatus of claim 15 wherein each said sole plate is substantially planar and is oriented angled away from a vertical orientation by a dorsiflexion angle configured to cause said toe end of each said sole plate to be closer to the person's head than said heel ends, said apparatus including means to adjust said dorsiflexion angle.

17. The apparatus of claim 16 wherein said means to adjust said dorsiflexion angle includes a wedge having a thin end oriented below a thick end, said dorsiflexion wedge oriented between said sole plate and said foot positioning support, said wedge including means to be slidably positioned at various different positions to alter said dorsiflexion angle.

18. The apparatus of claim 15 wherein each said foot positioning support is adjustably connected to a stance width section adjacent said center rail, said foot positioning supports being adjustably attached to the stance width section so that a spacing between the two foot positioning supports can be adjusted.

19. The apparatus of claim 18 wherein said stance width section includes means to be adjustably secured to said center rail, such that a distance between said stance width section and said sub-perineal spacer can be modified.

20. The apparatus of claim 15 wherein a substantially horizontal torso pad formed of resilient material is attached to said center rail on a side of said sup-perineal spacer opposite said foot positioning supports.

21. The apparatus of claim 15 wherein a knee support means is slidably attached to said center rail between said sub-perineal spacer and said foot positioning supports, said knee support means configured to extend away from said center rail to a location directly beneath a person's knees when the person is lying horizontally on top of said apparatus with the person's feet adjacent the foot positioning supports.

* * * * *